(12) United States Patent
Miyata

(10) Patent No.: US 6,592,834 B1
(45) Date of Patent: Jul. 15, 2003

(54) CALCIUM HYDROXIDE, A PROCESS FOR THE PRODUCTION THEREOF AND USE THEREOF

(75) Inventor: Shigeo Miyata, Kitakyushu (JP)

(73) Assignee: Kabushiki Kaisha Kaisui Kagaku Kenkyujo, Fukuoka-ken (JP)

( * ) Notice: Subject to any disclaimer, the term of this patent is extended or adjusted under 35 U.S.C. 154(b) by 0 days.

(21) Appl. No.: 09/638,873

(22) Filed: Aug. 15, 2000

(30) Foreign Application Priority Data

Aug. 19, 1999 (JP) .......................................... 11-232308
Jul. 4, 2000 (JP) ........................................ 2000/201733

(51) Int. Cl.⁷ ............................................... C01F 11/00
(52) U.S. Cl. ........................ 423/265; 423/636; 423/274
(58) Field of Search .................................. 423/635, 636, 423/265, 274; 524/399, 400, 436

(56) References Cited

U.S. PATENT DOCUMENTS

| | | | |
|---|---|---|---|
| 3,926,873 A | 12/1975 | Aishima et al. | |
| 5,223,239 A | * 6/1993 | Moran et al. | 423/640 |
| 5,422,092 A | * 6/1995 | Miyata | 423/594 |
| 5,466,740 A | * 11/1995 | Miyata | 423/599 |
| 5,492,685 A | 2/1996 | Moran et al. | |
| 5,653,795 A | 8/1997 | Brown | |

FOREIGN PATENT DOCUMENTS

| | | |
|---|---|---|
| EP | 0 614 948 | 9/1994 |
| JP | 9-110424 | * 4/1997 |
| WO | 97/10309 | 3/1997 |

* cited by examiner

*Primary Examiner*—Steven Bos
(74) *Attorney, Agent, or Firm*—Wenderoth, Lind & Ponack, L.L.P.

(57) ABSTRACT

Calcium hydroxide in which the average secondary particle diameter at a cumulative percentage of 50% by number in a particle size distribution is 2.0 μm or less and the BET specific surface area is 7 to 20 m²/g and which is surface-treated with 0.1 to 10% by weight of an anionic surfactant, its production process and its use.

6 Claims, No Drawings

CALCIUM HYDROXIDE, A PROCESS FOR THE PRODUCTION THEREOF AND USE THEREOF

BACKGROUND OF THE INVENTION

1. Field of the Invention

The present invention relates to a high-purity calcium hydroxide having fine particles and a high dispersibility in a resin, a process for the production thereof and a calcium hydroxide-containing resin composition containing said calcium hydroxide as an active ingredient for an acid-capturing agent. More specifically, it relates to calcium hydroxide which can work as a heat stabilizer for a resin, prevent the occurrence of dioxin or the like, prevent the corrosion of a processing machine or impart antifungal properties owing to the capture of an acid substance such as hydrochloric acid, generated from a resin or garbage at a processing or burning time, at high yields by incorporating a high-purity calcium hydroxide having fine particles and a high dispersibility, as an active ingredient, into a resin such as polyvinyl chloride or polyethylene, a process for the production thereof and a calcium hydroxide-containing resin composition containing said calcium hydroxide as an active ingredient for an acid-capturing agent.

2. Description of the Prior Art

A conventional calcium hydroxide has large primary particles (crystal) as large as about 1 $\mu$m to several $\mu$m, and these particles agglomerate strongly to form large secondary particles (the average secondary particle diameter at a cumulative percentage of 50% is about 4 to 20 $\mu$m). Further, the above calcium hydroxide is very unstable, and it has the problem that the calcium hydroxide is easily reacted with a carbonic acid gas in the air to convert to calcium carbonate. When the conventional calcium hydroxide is added in a resin, therefore, the calcium hydroxide is remarkably poor in dispersibility in the resin. For example, when a resin composition containing the calcium hydroxide is molded to a film, the surface of the film is rough, and further, the film is colored to have a puce color due to large amounts of impurities such as Fe or Mn. Further, the reactivity of the calcium hydroxide with an acid such as hydrogen chloride generated from polyvinyl chloride is impaired since the primary particles and the secondary particles are large. Therefore, a corresponding amount of the calcium hydroxide should be further added to the resin. When the amount of the calcium hydroxide increases, inherent properties of a resin are impaired, which extremely decreases a value as a commodity product.

SUMMARY OF THE INVENTION

It is an object of the present invention to provide a fine-particle, high-dispersibility and high-purity calcium hydroxide of which the primary particles and secondary particles are fine, and which is prevented from converting to calcium carbonate, and a process for the production thereof.

It is another object of the present invention to provide a calcium hydroxide (acid-capturing agent)-containing resin composition which has a high dispersibility, a high purity and high whiteness and which is excellent in the appearance of a molded article, mechanical strength, thermal stability, antifungal properties and acid-capturing properties.

According to the present invention, there is provided a calcium hydroxide in which the average secondary particle diameter at a cumulative percentage of 50% by number in a particle size distribution is 2.0 $\mu$m or less, preferably 0.1 to 1.5 $\mu$m, particularly preferably 0.5 to 1.1 $\mu$m, and the BET specific surface area is 7 to 20 m$^2$/g, preferably 8 to 20 m$^2$/g, more preferably 9 to 18 m$^2$/g, particularly preferably 10 to 15 m$^2$/g. According to the present invention, there is provided a calcium hydroxide which is surface-treated with 0.1 to 10% by weight, preferably 0.5 to 5% by weight, more preferably 1 to 5% by weight, of an anionic surfactant.

According to the present invention, further, there is provided a calcium hydroxide-containing resin composition obtained by incorporating 0.1 to 100 parts by weight, preferably 0.2 to 50 parts by weight, particularly preferably 0.5 to 20 parts by weight, of said calcium hydroxide as an active ingredient into 100 parts by weight of a synthetic resin.

According to the present invention, further, there is provided a process for the production of the calcium hydroxide as recited above, comprising adding a water-soluble calcium salt aqueous solution to an aqueous solution containing at least one equivalent of alkali metal hydroxide to calcium with stirring, allowing the mixture to react at 30 to 90° C., preferably 40 to 90° C., then aging the resultant mixture at 40 to 120° C., preferably 40 to 80° C., for preferably about 0.1 to 2 hours to synthesize calcium hydroxide, and then adding an aqueous solution of an anionic surfactant in an amount of 0.1 to 10% by weight based on the calcium hydroxide at a temperature where the anionic surfactant is soluble or at a higher temperature with stirring, to surface-treat the calcium hydroxide.

According to the present invention, further, there is provided a process for the production of the calcium hydroxide as recited above, comprising wet-pulverizing a slaked lime obtained by slaking a quicklime (calcium oxide) having small contents of impurities such as silicone dioxide, alumina and ferric oxide ($Fe_2O_3$), then adding an anionic surfactant to the wet-pulverized slaked lime in a water medium with stirring to surface-treat the slaked lime, or adding the anionic surfactant before the wet-pulverization and carrying out the wet-pulverization and the surface-treatment at the same time.

DETAILED DESCRIPTION OF THE INVENTION

In the calcium hydroxide used in the present invention, the secondary particles of the calcium hydroxide are required to be fine particles, and therefore, the primary particles of the calcium hydroxide are also required to be fine particles. These states of the primary and secondary particles make it possible to give a good appearance of a molded article and to improve various properties such as mechanical strength and high acid-capturing properties.

Concerning the primary particles, at least the average particle diameter thereof is 1 $\mu$m or less, preferably 0.5 $\mu$m or less. The average particle diameter of the primary particles is measured by a scanning electron microscope (SEM) method. The secondary particles are ultrasonically treated in an isopropyl alcohol solvent for five minutes to be dispersed, and then, the average particle diameter of the secondary particles is determined by a particle size distribution measured by a laser diffraction method. The average secondary particle diameter at a cumulative percentage of 50% by number in the particle size distribution is 2.0 $\mu$m or less, preferably 0.1 to 1.5 $\mu$m, particularly preferably 0.5 to 1.1 $\mu$m. Concerning the secondary particles, besides the above definition in case of the cumulative percentage of 50% by number, the average secondary particle diameter at a cumulative percentage of 90% by number is preferably 8 μm or less, more preferably 5 μm or less, furthermore preferably 4 μm or less, particularly preferably 2 μm or less.

The BET specific surface area almost corresponds to the size of the primary particles. The BET specific surface area of the calcium hydroxide of the present invention is 7 to 20 $m^2/g$, preferably 8 to 20 $m^2/g$, more preferably 9 to 18 $m^2/g$, particularly preferably 10 to 15 $m^2/g$. When the BET specific surface area is larger than 20 $m^2/g$, the calcium hydroxide is likely to agglomerate and the viscosity of a resin becomes too high so that it is difficult to knead a resin composition containing the calcium hydroxide and the moldability of the resin composition is deteriorated. Conversely, when the BET specific surface area is smaller than 7 $m^2/g$, the primary particles become too large so that activities such as acid-capturing properties are decreased.

The calcium hydroxide used in the present invention may be produced by the following two methods. In the first method, the calcium hydroxide can be produced by adding an aqueous solution of a water-soluble calcium salt such as calcium chloride or calcium nitrate into an aqueous solution of alkali metal hydroxide such as sodium hydroxide and potassium hydroxide in an alkali ratio of at least one equivalent, preferably 1.1 to 1.3 equivalent, to calcium at 30 to 90° C., preferably 40 to 90° C., with stirring, allowing the mixture to react, then aging the reaction mixture under heat at preferably about 40 to 120° C., particularly preferably about 40 to 80° C., for about 0.1 to 2 hours and adding an anionic surfactant to the aged mixture to carry out a surface-treatment.

The second method is a method of reacting quicklime obtained by the calcination of natural lime having a high purity with water at a temperature of preferably about 60 to 90° C. to form slaked lime and, preferably, wet-pulverizing it with a ball-mill. In this case, the diameter of a ball consisting of alumina, zirconia, glass or the like is about 2 mm or less, preferably 0.5 to 2mm, and the use of such a ball is preferred. The period of time for pulverization differs depending upon a kind of a machine, while it is about 1 to 20 hours. The surface-treatment may be carried out before or after the pulverization treatment. As a ball mill machine, there is used a rolling ball mill, a vibration ball mill, or a stirring mill such as a screw type stirring mill, a circulation tube type stirring mill, a stirring tank type stirring mill or an annular type stirring mill. The treatment is carried out in a batch treatment or a continuous treatment. Before or after the pulverization treatment, rough components are removed through a screen of preferably 100 to 500 meshes. As a high-purity quicklime, there is preferably used a quicklime having a silicon dioxide content of 0.2% by weight or less, particularly preferably 0.1% by weight or less, an alumina content of 0.04% by weight or less, particularly preferably 0.02% by weight or less, and a ferric oxide content of 0.02% by weight or less, particularly preferably 0.01% by weight or less.

The calcium hydroxide produced by any one of the above two methods can be surface-treated as follows. An aqueous solution in which an anionic surfactant in an amount of 0.1 to 10% by weight, preferably 0.5 to 5% by weight, based on the weight of the calcium hydroxide is dissolved, is added to the calcium hydroxide in a state where it is stirred and dispersed in water at a temperature (about 40° C.) where the anionic surfactant is soluble or at a higher temperature, to surface-treat the calcium hydroxide. Thereafter, there can be carried out general treatments selected from filtration, washing with water, drying, pulverization, classification and the like as required. The surface-treatment is effective at dispersing the calcium hydroxide in a resin and at preventing the calcium hydroxide from converting to calcium carbonate due to carbonization. Therefore, the surface-treated calcium hydroxide is used. When calcium hydroxide is converted to calcium carbonate, activities such as acid-capturing properties are extremely decreased.

As a surface-treating agent used in the present invention, there is used an aqueous solution of an anionic surfactant or a phosphoric acid ester which works as anion in the aqueous solution. Examples of preferred surface-treating agents include alkali metal salts of saturated or unsaturated fatty acids having about five or more carbon atoms, such as sodium caprylate, sodium caprinate, sodium laurate, sodium stearate, sodium oleate, and sodium behenate; phosphoric acid esters of alkali metal salts or amine salts such as lauryl acid phosphate, oleyl acid phosphate and stearyle acid phosphate; sulfonates such as sodium alkylbenzene sulfonate and sodium alkyl sulfonate; and sulfates such as alkyl ether sulfate, alkyl aryl ether sulfate, alkylamide sulfate and alkyl sulfate. Of these, particularly preferred is an alkali metal salt of a higher fatty acid.

The resin used in the present invention includes the following examples. The examples include no-halogen-containing thermoplastic resins such as polyethylene, a copolymer of ethylene and other α-olefin, a copolymer of ethylene and vinyl acetate, ethyl acrylate, or methyl acrylate, polypropylene, a copolymer of polypropylene and other α-olefin, polybutene-1, polystyrene, a copolymer of styrene and acrylonitrile, a copolymer of ethylene and propylene-diene rubber or butadiene, vinyl acetate, polyacrylate, polymethacrylate, polyurethane, polyester, polyether, and polyamide; chlorine-containing thermoplastic resins such as polyvinyl chloride, polyvinylidene chloride, chlorinated polyethylene, chlorinated polypropylene, a copolymer of vinyl chloride and vinyl acetate, a copolymer of vinyl chloride and ethylene, a copolymer of vinyl chloride and propylene, a copolymer of vinyl chloride and styrene, a copolymer of vinyl chloride and isobutylene, a copolymer of vinyl chloride and vinylidene chloride, a copolymer of vinyl chloride, styrene and maleic anhydride, a copolymer of vinyl chloride, styrene and acrylonitrile, a copolymer of vinyl chloride and butadiene, a copolymer of vinyl chloride and isoprene, a copolymer of vinyl chloride and chlorinated propylene, a copolymer of vinyl chloride, vinylidene chloride and vinyl acetate, a copolymer of vinyl chloride and an acrylic acid ester, a copolymer of vinyl chloride and a methacrylic acid ester, a copolymer of vinyl chloride and acrylonitrile, and a copolymer of vinyl chloride and any one of various vinyl ethers; halogen-containing rubbers such as fluorine-containing rubber, ethylene tetrafluoride, propylene rubber, chlorosulfonated polyethylene rubber, epichlorohydrin rubber, chloroprene rubber and brominated butyl rubber; and thermosetting resins such as a phenol resin, a melamine resin, an epoxy resin, an unsaturated polyester resin and an alkyd resin.

Of the above resins, particularly preferred are a halogen-containing resin such as polyvinyl chloride or polyvinylidene chloride and polyolefin such as polyethylene or polypropylene.

In the present invention, no special limitation is imposed upon the method of mixing and kneading the resin and the calcium hydroxide. Any mixing means may be adopted, so long as the means can uniformly mix both the components. For example, it includes a single-screw or two-screw extruder, a roll and a Banbury mixer. No special limitation is also imposed upon the molding method. Any known method may be adopted depending upon the kind of a resin and the kind of a desired molded article. For example, it includes an injection molding, an inflation film molding, a T-dice film molding, a calender molding, an extrusion molding, a blow molding, a press molding, a rotation molding, a sheet forming molding, a transfer molding, a laminate molding and a vacuum molding.

The calcium hydroxide-containing resin of the present invention may contain generally-used various additives other than the calcium hydroxide as desired. Examples of the additives include an antioxidant, an ultraviolet light absorber, a light stabilizer, a plasticizer, an antistatic agent, a pigment, a lubricant, a forming agent, a filler, a reinforcing agent, a crosslinker, a vulcanizing agent, a thermal stabilization assistant, and a processing stabilizer. The thermal stabilization assistant includes an organic acid salt of zinc such as zinc stearate, β-diketone such as dibenzoyl methane and stearoyl benzoyl methane, polyhydric alcohols such as pentaerythritol, dipentaerythritol and trimethylol propane, perchlorates such as sodium perchlorate, perchlorate type hydrotalcite, $CO_3$ type hydrotalcite, and phosphite.

The calcium hydroxide-containing resin of the present invention can be utilized in the following fields. When the resin is a halogen-containing resin such as polyvinyl chloride, the calcium hydroxide-containing resin of the present invention captures and neutralizes an acid substance such as hydrogen chloride occurring at a processing time or a burning (incinerating) time, whereby the calcium hydroxide-containing resin of the present invention can be used as a heat stabilizer for the resin, as an inhibitor of the occurrence of dioxin or as an inhibitor of deterioration of an incinerator due to an acid. For example, when the calcium hydroxide-containing resin of the present invention is used for a trash bag made of polyethylene or polypropylene or for a food-packing material, it serves to prevent dioxin from occurring by capturing an acid substance, such as a halogenated hydrogen, which occurs from garbage at a time of the incineration of the garbage. Further, owing to the incorporation of the calcium hydroxide-containing resin of the present invention in a food-packing material, antifungal properties appear so that the calcium hydroxide-containing resin of the present invention can be utilized for a food-packing material having the function of keeping freshness. When the calcium hydroxide-containing resin of the present invention is incorporated in a film for agriculture, for example, it can be utilized for preventing the deterioration of activity of HALS (hindered-amine-containing light stabilizer) due to an agricultural chemical. Further, it can be utilized for inactivating a residue of a Ziegler catalyst or a metallocene catalyst in polyolefin and utilized as a halogen-capturing agent. For example, it can be also utilized as an inhibitor of an acetic acid smell of a vinyl acetate-conataining resin. For example, it can be also utilized as a vulcanizing agent or a vulcanization promoter for a fluorine-containing rubber and a brominated butyl rubber. Furthermore, it can be also utilized as a thickening agent for FRP.

The present invention will be explained more in detail with reference to Examples hereinafter. In each Example, "%" stands for "% by weight" unless otherwise specified.

EXAMPLE 1

2.08 liters of a 5 mol/liter sodium hydroxide aqueous solution having a temperature of 30° (1.3 equivalents of alkali to Ca) was added to a reaction tank made of stainless steel and having a volume of 5 liters, 2 liters of a 2 mol/liter calcium chloride aqueous solution (30° C.) was added thereto over about two minutes with stirring, and the mixture was allowed to react.

The reaction mixture was heated with a gas cooker, temperature-increased up to about 45° C. and maintained for about 20 minutes. Then, about 200 milliliters of an aqueous solution (about 45° C.) in which 10 g of sodium laurate (corresponding to 3% by weight based on the weight of calcium hydroxide) having a purity of 89% was dissolved was added with stirring to carry out a surface-treatment. Then, the resultant mixture was filtrated, washed with water, and dried at about 120° C. The resultant material was pulverized with an atomizer, to obtain a powder. The powder was treated in isopropyl alcohol with an ultrasonic for about five minutes to be dispersed therein, then the particle size distribution of secondary particles was measured with a particle size distribution measuring device (supplied by Seishin) according to a laser diffraction method. As a result thereof, the average secondary particle diameter at a cumulative percentage of 10% in the particle size distribution was 0.56 μm, the average secondary particle diameter at a cumulative percentage of 50% was 1.00 μm and the average secondary particle diameter at a cumulative percentage of 90% was 6.23 μm. The average primary particle diameter was about 0.17 μm. The average primary particle diameter was measured by a scanning electron microscope method. The amount of lauric acid was measured by a gravimetric method of dissolving a sample in hydrochloric acid, extracting lauric acid with ethyl ether and drying it. The amount of lauric acid was 2.1%. The BET specific surface area was 15 $m^2$/g. As a result of an X-ray fluorometric analysis, each of $SiO_2$ and $Al_2O_3$ was independently 0.01% or less. $Fe_2O_3$ was 0.003%.

50 parts by weight of dioctyl phthalate (DOP), 0.2 part by weight of zinc stearate, and 50 parts by weight of the calcium hydroxide produced by the above method were added to 100 parts by weight of polyvinyl chloride (supplied by Shin-Etsu Chemical Co., Ltd., TK-1300). The mixture was kneaded with an open roll for five minutes at about 170° C. to prepare a sheet having a thickness of about 1 mm. As a result of an estimate by a visual observation, the sheet had a white color, and the calcium hydroxide was fully dispersed. Part having an amount of about 0.7 g was cut off from the sheet. The above part was further cut off to small sizes with a pair of scissors and placed in an alumina tray. The tray was placed in an alumina tube having a diameter of 20 mm and a length of 700 mm. The temperature in the alumina tube was increased up to 700° C. under an air current of about 110 ml/minute, and maintained for 20 minutes. HCl occurring during it was absorbed in three pieces of wash bottles which are connected to each other and contain 50 milliliters of a 0.02 mol/liter NaOH aqueous solution. The absorption solution was neutralized with nitric acid, then silver nitrate in an excess amount was added thereto, and the resultant mixture was back-titrated with ammonium thiocyanate, to determine the generation amount of hydrochloric acid per 1 g of the sample. As a result thereof, the generation amount of hydrochloric acid was 30 mg/g, and the rate of capturing hydrochloric acid was 90%, (calculated from a hydrochloric acid generation amount of 291 mg/g in the case of containing no calcium hydroxide).

EXAMPLE 2

120 g of a commercially-available high-purity quicklime ($SiO_2$=0.014%, $Al_2O_3$=0.007%, $Fe_2O_3$=0.022%) calcined at about 900° C. was added to 1 liter of water having a temperature of about 70° C., and the mixture was stirred for about 30 minutes, to obtain a slurry. The slurry was passed through a 200-mesh screen, and then placed in a ball mill having a volume of 3 liters. Further, 2.5 kg of alumina balls having a diameter of 2 mm each were placed therein, and a pulverization was carried out for 10 hours. The so-treated material was moved through a 200-mesh screen to a reaction tank made of stainless steel and having a volume of 5 liters and heated up to 60° C. 100 ml of an aqueous solution (about 60° C.) in which 6.6 g of sodium stearate having a purity of 90% was dissolved was added with stirring to carry out the surface-treatment. Then, the surface-treated material was filtrated, dried and pulverized. In the particle size distribution of the so-obtained material, the average secondary particle diameter at a cumulative percentage of 10% was 0.58 $\mu$m, the average secondary particle diameter at a cumulative percentage of 50% was 1.10 $\mu$m, and the average secondary particle diameter at a cumulative percentage of 90% was 3.90 $\mu$m. The BET specific surface area was 10 $m^2/g$. The content of stearic acid was 3.2%. The average primary particle diameter was about 0.27 $\mu$m. Each of $SiO_2$ and $Al_2O_3$ was independently 0.01% or less. $Fe_2O_3$ was 0.02%.

The above calcium hydroxide was used to measure the generation amount of hydrochloric acid in the same manner as in Example 1. As a result, the generation amount of hydrochloric acid was 35 mg/g, and the rate of capturing hydrochloric acid was 88%.

Comparative Example 1

A commercially-available slaked lime ($SiO_2$=0.31%, $Al_2O_3$=0.03%, $Fe_2O_3$=0.08%) was surface-treated with sodium laurate in an amount of 3% in the same manner as in Example 1. Then, the resultant material was filtrated, dried and pulverized. In the so-obtained material, the average secondary particle diameter at a cumulative percentage of 10% in a particle size distribution was 0.92 $\mu$m, the average secondary particle diameter at a cumulative percentage of 50% was 5.62 $\mu$m, and the average secondary particle diameter at a cumulative percentage of 90% was 12.75 $\mu$m. The average primary particle diameter was about 1.52 $\mu$m. The content of lauric acid was 2.0%. The BET specific surface area was 4.2 $m^2/g$. This material was used to measure the generation amount of hydrochloric acid in the same manner as in Example 1. As a result, the generation amount of hydrochloric acid was 115 mg/g, and the rate of capturing hydrochloric acid was 59%.

EXAMPLE 3

40 parts by weight of the calcium hydroxide surface-treated with sodium laurate, obtained in Example 1, and 60 parts by weight of a low-density polyethylene (LDPE) were mixed, and then a master batch was prepared from the mixture with a two-screw extruder. 40 parts by weight of the master batch and 60 parts by weight of LDPE were mixed, and the mixture was molded by an inflation method to obtain a film having a thickness of 40 $\mu$m and a width of 75 cm. The film was estimated by a visual observation. As a result, there was found no granular structure caused by the dispersion failure of the calcium hydroxide, the film had a white color and both gloss and transparency were good. The film was measured for tensile strength and elongation according to JISZ1702. Table 1 shows the results.

The relationship between a trash bag (made of polyethylene), the amount of garbage and the content of a hydrochloric acid source in a town-garbage is said to be respectively 50 g (one bag), 3 kg and 0.4% [Thomas et al., Organohalogen Compound.20,367(1994)]. Thereat, 50 g of the polyethylene film containing 16% of the surface-treated calcium hydroxide and obtained by the above method and polyvinyl chloride in an amount of about 20 g which corresponds to a hydrochloric acid content of 12 g (3 kg×0.004) were kneaded with an open roll for five minutes at about 170° C. to prepare a sheet having a thickness of about 1 mm. The sheet was used as a sample, and measured for the generation amount of hydrochloric acid in the same manner as in Example 1. The generation amount of hydrochloric acid was 35.7 mg/g, and the rate of capturing hydrochloric acid was 76%, (calculated from a hydrochloric acid generation amount of 148 mg/g in the case of using 50 g of polyethylene containing no calcium hydroxide)

Comparative Example 2

The same commercially-available calcium hydroxide as that used in Comparative Example 1 was surface-treated in the same manner as in Comparative Example 1. The surface-treated calcium hydroxide was used to prepare a master batch of a low-density polyethylene (40% of the surface-treated calcium hydroxide contained) in the same manner as in Example 3. Then, the master batch was mixed with a low-density polyethylene in a master batch: low-density polyethylene ratio of 40:60. The mixture was molded by an inflation method to obtain a film having a thickness of 40 $\mu$m (16% of the surface-treated calcium hydroxide contained). The film had rough surface, it was poor in transparency, it had no gloss, and it had a brown color. 50 g of the film was kneaded with polyvinyl chloride in the same amount ratio as in Example 3, to obtain a sheet. The sheet was measured for the generation amount of hydrochloric acid. As a result, the generation amount of hydrochloric acid was 99 mg/g, and the rate of capturing hydrochloric acid was 33%.

TABLE 1

Tensile strength and elongation of a film

| | Tensile strength at break (kg/cm$^2$) | | Elongation (%) | |
| --- | --- | --- | --- | --- |
| | Length | Width | Length | Width |
| Example 3 | 185 | 210 | 330 | 650 |
| Comparative Example 2 | 150 | 158 | 390 | 550 |
| Control (polyethylene alone) | 170 | 170 | 320 | 660 |

EXAMPLE 4

A tank having a volume of 4 liters was charged with 1.1 liters of a 4 mol/liter sodium hydroxide aqueous solution (1.1 equivalents of alkali to Ca). 2 liters of a 1 mol/liter calcium chloride aqueous solution having a temperature of about 40° C. was entirely added to the tank at about 40° C. over about five minutes with stirring. Then, the mixture in the tank was heated up to about 60° C., and the mixture was maintained at this temperature for 20 minutes. Then, 100 milliliters of an about 60° C.-hot aqueous solution in which 3.4 g of sodium laurate (purity 87%) was dissolved was added with stirring. After the entire amount of the above aqueous solution was added, the stirring was continued for about five minutes at about 60° C. Then, the resultant mixture was filtrated, dried and pulverized. The so-obtained material had a BET specific surface area of 12 $m^2/g$ and an average primary particle diameter of about 0.22 $\mu$m. The particle size distribution thereof was measured in the same manner as in Example 1. In the particle size distribution, the average secondary particle diameter at a cumulative percentage of 10% was 0.56 μm, the average secondary particle diameter at a cumulative percentage of 50% was 0.99 μm, and the average secondary particle diameter at a cumulative percentage of 90% was 4.53 μm. The amount of a surface-treating agent was measured in the same manner as in Example 1, and the amount of a surface-treating agent was 1.6% by weight as lauric acid. Each of $SiO_2$ and $Al_2O_3$ as impurities was respectively 0.01% or less, and $Fe_2O_3$ was 0.002%.

EXAMPLE 5

A slurry was obtained by the same reaction as that in Example 1. The slurry was poured in an autoclave having a volume of 5 liters, and hydrothermally treated at 120° C. for 2 hours. The hydrothermally-treated slurry was taken out, and about 100 milliliters of an about 60° C.-hot aqueous solution in which 4.1 g of sodium orate (purity 90%) was dissolved, was added at about 60° C. with stirring. After the entire amount of the aqueous solution was added, the stirring was continued for about 30 minutes at about 60° C. Then, the resultant mixture was filtrated, dried and pulverized. The content of oleic acid was analyzed in the same manner as in Example 1. As a result, it was 2.1% by weight. The average primary particle diameter thereof was about 0.33 μm. The average secondary particle diameter at a cumulative percentage of 10% in a particle size distribution was 0.42 μm, the average secondary particle diameter at a cumulative percentage of 50% was 1.05 μm. and the average secondary particle diameter at a cumulative percentage of 90% was 3.26 μm. The BET specific surface area was 8.1 $m^2/g$. Concerning the amounts of impurities, each of $SiO_2$ and $Al_2O_3$ was respectively 0.01% or less, and $Fe_2O_3$ was 0.002%.

Comparative Example 3

Example 5 was repeated except that no surface-treatment was carried out. As a result, a product had a BET specific surface area of 10 $m^2/g$. The average secondary particle diameter thereof at a cumulative percentage of 10% in a particle size distribution was 0.75 μm, the average secondary particle diameter at a cumulative percentage of 50% was 3.62 μm, and the average secondary particle diameter at a cumulative percentage of 90% was 31.58 μm. The amounts of impurities were almost the same amounts as those in Example 5.

EXAMPLE 6

| | |
|---|---|
| Polyvinyl chloride (TK-700, supplied by Shin-Etsu Chemical Co., Ltd) | 100 parts by weight |
| stearoyl benzoyl methane (SBM) | 0.15 part by weight |
| zinc stearate | 0.3 part by weight |
| pentaerythritol | 0.2 part by weight |
| heat stabilizer (calcium hydroxide, etc.) | 1.0 part by weight |

A hard polyvinyl chloride containing the above components was uniformly mixed and then, it was kneaded with an open roll for 3 minutes at 165° C., to prepare a sheet having a thickness of about 1 mm. The sheet was placed in a Geer oven set at 185° C., and it was estimated for a thermal stability. Table 2 shows the results.

Comparative Example 4

In Example 6, the calcium hydroxide of the present invention was replaced with a calcium hydroxide obtained by surface-treating a commercially available calcium hydroxide (4-1), calcium hydroxide synthesized by the method of Example 3 (4-2), octyl tin mercaptide which was a PVC stabilizer (4-3), and calcium stearate (4-4), shown in Table 2. These cases were estimated. Table 2 shows the results.

TABLE 2

Thermal stability test

| | Stabilizer | Dispers-ibility[1] | Trans-par-ency[2] | Initial color[3] | Thermal stability (minute)[4] |
|---|---|---|---|---|---|
| Example 6-1 | Calcium hydroxide obtained in Example 1 | good | good | no color | 60 |
| Example 6-2 | Calcium hydroxide obtained in Example 2 | good | good | no color | 60 |
| Example 6-3 | Calcium hydroxide obtained in Example 4 | good | good | No color | 60 |
| Example 6-4 | Calcium hydroxide obtained in Example 5 | excellent | good | excellent | 50 |
| Comparative Example 4-1 | Calcium hydroxide in Comparative Example 1 | White granular structure due to dispersion failure | poor | light reddish yellow | 45 |
| Comparative Example 4-2 | Calcium hydroxide in Comparative Example 3 | White granular structure due to dispersion failure | Slightly poor | no color | 50 |
| Comparative Example 4-3 | octyl tin mercaptide | good | good | no color | 20 |
| Comparative Example 4-4 | Calcium stearate | good | good | good | 40 |

[1] and [2]A black paper sheet was placed below the sheet obtained in one of Examples and Comparative Examples and dispersibility and transparency were estimated by a visually observation.
[3]Before the sheet was placed in a Geer oven, it was estimated by a visually observation.
[4]A period of time taken until the sheet was blackened.

EXAMPLE 7

| | |
|---|---|
| Polyvinyl chloride (TK-700, supplied by Shin-Etsu Chemical Co., Ltd) | 100 parts by weight |
| zinc stearate | 0.4 part by weight |
| dipentaerythritol | 0.2 part by weight |
| perchlorate type hydrotalcite (alcanizer-5, supplied by Kyowa Chemical Co., Ltd) | 0.02 part by weight |
| heat stabilizer (calcium hydroxide, etc.) | 1.0 part by weight |

A heat stabilizer (acid-capturing agent) shown in Table 3 was mixed with the above components other than the heat stabilizer in the above amounts, and the mixture was uniformly mixed. Then, it was kneaded with an open roll for 3 minutes at 180° C., to prepare a sheet having a thickness of about 1 mm. The sheet was placed in a Geer oven set at 185° C., and it was estimated for a thermal stability. Table 3 shows the results. Concerning properties required for the heat stabilizer, the heat stabilizer was required to be non-poisonous and a low price, to have good dispersibility, to be almost free from coloration, and to give a long period of time before blackening.

Comparative Example 5

In Example 7, the calcium hydroxide of the present invention as a heat stabilizer was replaced with a calcium hydroxide obtained by surface-treating a commercially available calcium hydroxide used in Comparative Example 1 (5-1), lead stearate (5-2), and A type zeolite (5-3). These cases were estimated. Table 3 shows the results.

TABLE 3

Thermal stability test

| | Stabilizer | Dispers-ibility[1] | Trans-par-ency[2] | Initial color[3] | Thermal stability (minute)[4] |
|---|---|---|---|---|---|
| Example 7-1 | Calcium hydroxide obtained in Example 1 | good | good | no color | 80 |
| Example 7-2 | Calcium hydroxide obtained in Example 2 | good | good | no color | 70 |
| Comparative Example 5-1 | Calcium hydroxide in Comparative Example 1 | White granular structure due to dispersion failure | poor | light reddish yellow | 50 |
| Comparative Example 5-2 | Lead stearate | good | Slightly poor | no color | 50 |
| Comparative Example 5-3 | A type zeolite | good | poor | light reddish yellow | 40 |

[1] and [2] A black paper sheet was placed below the sheet obtained in one of Examples and Comparative Examples and dispersibility and transparency were estimated by a visually observation.
[3] Before the sheet was placed in a Geer oven, it was estimated by a visually observation.
[4] A period of time taken until the sheet was blackened.

EXAMPLE 8

The same master batch of calcium hydroxide as that obtained in Example 3 was molded by an inflation method to obtain a film having a thickness of 40 μm. In this Example, the master batch: low-density polyethylene amount ratio was 5:95, and the content of the surface-treated calcium hydroxide n the film was 2% by weight. This film was cut to a size having a length of 5 cm and a width of 5 cm. According to a film adhesion method, *Escherichia coli* and staphylococcus aureus were measured for the increase and decrease of the number of each fungus after cultivation at 35° C. for 24 hours, whereby antifungal properties were estimated. Table 4 shows the results.

Comparative Example 6

The same commercially-available calcium hydroxide as that used in Comparative Example 1 was surface-treated in the same manner as in Comparative Example 1. The surface-treated calcium hydroxide was mixed with a low-density polyethylene in a calcium hydroxide: low-density polyethylene weight ratio of 40:60. Thereafter, a master batch was prepared similarly to Example 3. Then, 5 parts by weight of the master batch was mixed with 95 parts by weight of a low density polyethylene, and the mixture was molded by an inflation method to obtain a film having a thickness of 40 μm. Then, antifungal properties were estimated. Table 4 shows the results.

TABLE 4 antifungal properties of a calcium hydroxide-containing low-density polyethylene film

| | *Escherichia coli* | | *staphylococcus aureus* | |
|---|---|---|---|---|
| | Number of fungus/ml | Rate of decreasing fungus (%) | Number of fungus/ml | Rate of decreasing fungus (%) |
| Example 8 | $5.5 \times 10^3$ | 99.7 | $1.8 \times 10^3$ | 98.6 |
| Comparative Example 6 | $8.6 \times 10^5$ | 46.3 | $5.6 \times 10^4$ | 56.9 |
| Control film | $1.6 \times 10^6$ | — | $1.3 \times 10^5$ | — |

Effect of the Invention

According to the present invention, the calcium hydroxide as an acid-capturing agent is highly dispersed in a resin in a state of fine particles. As a result, there can be provided a resin composition having excellent appearance (white color, transparency, gloss, surface smoothness, etc.) of a molded article and mechanical strength. Further, the above resin composition can capture an acid substance such as hydrochloric acid, which occurs when polyvinyl chloride or the like is burnt, up to a high temperature at a remarkably high capturing rate which is almost twice as high as the capturing rate of a conventional calcium hydroxide. As a result, it is expected to prevent the occurrence of a harmful substance, e.g., dioxin. Further, the calcium hydroxide of the present invention shows excellent properties as a heat stabilizer for a halogen-containing resin such as polyvinyl chloride or as an antifungus agent.

What is claimed is:

1. A process for the production of a material consisting essentially of calcium hydroxide, in which the average secondary particle diameter at a cumulative percentage of 50% by number in a particle size distribution is 2.0 μm or less and the BET specific surface area is 7 to 20 m$^2$/g and which is surface-treated with 0.1 to 10% by weight of an anionic surfactant, said process consisting essentially of adding a water-soluble calcium salt aqueous solution to an aqueous solution containing at least one equivalent of alkali metal hydroxide to calcium with stirring, allowing the mixture to react at 30 to 90° C., then aging the resultant mixture at 40 to 120° C. to produce calcium hydroxide, and adding an aqueous solution of 0.1 to 10% by weight, based on the calcium hydroxide, of an anionic surfactant at a temperature where the anionic surfactant is soluble or at a higher temperature, with stirring, to surface-treat the calcium hydroxide, thereby obtaining said material consisting essentially of calcium hydroxide.

2. The process for the production of the calcium hydroxide according to claim 1, wherein the temperature for the above aging is 40 to 80° C.

3. The process for the production of the calcium hydroxide according to claim 1, wherein the period of time for the above aging is 0.1 to 2 hours.

4. The process according to claim 1, wherein the average secondary particle diameter at a cumulative percentage of 50% by number in the particle size distribution is 0.1 to 1.5 μm and the BET specific surface area is 8 to 15 m$^2$/g.

5. The process according to claim 1, wherein the average secondary particle diameter at a cumulative percentage of 50% by number in the particle size distribution is 0.1 to 1.5 μm and the BET specific surface area is 10 to 15 m$^2$/g.

6. The process according to claim 1, wherein the average secondary particle diameter at a cumulative percentage of 90% by number in the particle size distribution is 8 μm or less.

* * * * *